United States Patent [19]

Berry et al.

[11] Patent Number: 5,324,444
[45] Date of Patent: Jun. 28, 1994

[54] PROCESS FOR PREPARING A PERFUME CAPSULE COMPOSITION

[75] Inventors: Gregory Berry; John M. Marynowski; Kermit W. Kinne, all of Cincinnati, Ohio

[73] Assignee: The Procter & Gamble Company, Cincinnati, Ohio

[21] Appl. No.: 43,963

[22] Filed: Apr. 12, 1993

Related U.S. Application Data

[63] Continuation of Ser. No. 811,094, Dec. 20, 1991, abandoned.

[51] Int. Cl.$^5$ .............................................. C11D 17/00
[52] U.S. Cl. .......................... 252/174.11; 252/174.13; 252/174.25; 252/381
[58] Field of Search .................... 252/174.11, 174.13, 252/174.25, 381-385

[56] References Cited

U.S. PATENT DOCUMENTS

| | | | |
|---|---|---|---|
| 3,494,872 | 2/1970 | Maierson et al. | 252/316 |
| 4,145,184 | 3/1979 | Brain et al. | 8/137 |
| 4,446,032 | 5/1984 | Munteanu et al. | 512/4 |
| 5,066,419 | 11/1991 | Walley et al. | 252/174.11 |

*Primary Examiner*—Robert Kunemurd
*Assistant Examiner*—C. Everhart
*Attorney, Agent, or Firm*—Mary P. McMahon; Jacobus C. Rasser; Kathleen M. Harleston

[57] ABSTRACT

A method for preparing a free flowing perfume capsule composition with enhanced performance and stability from slurries containing perfume capsules is described. A process comprising removing water from the slurry to form a wet cake, combining silicone dioxide or aluminosilicate to the wet cake to fluidize the wet cake and removing additional water from the fluidized wet cake to form free flowing perfume capsules is preferred.

16 Claims, No Drawings

PROCESS FOR PREPARING A PERFUME CAPSULE COMPOSITION

This is a continuation of application Ser. No. 07/811,094, filed on Dec. 20, 1991, now abandoned.

TECHNICAL FIELD

This invention relates to a method for preparing a perfume capsule composition using silicon dioxide or aluminosilicate. More particularly, this invention relates to a method for preparing a free flowing perfume capsule composition which improves the drying time of a wet cake containing perfume capsules and enhances perfume performance and stability.

BACKGROUND OF THE INVENTION

Detergent compositions containing perfume are well known in the art. The perfume is ordinarily mixed or admixed with the liquid or granular detergent composition. Perfume makes the composition more aesthetically pleasing to the consumer, and in some cases it imparts a pleasant fragrance to surfaces. Most consumers have come to expect detergent compositions to have a pleasing odor.

Because perfumes are made of a combination of volatile compounds, perfume can be continuously emitted from simple solutions and dry mixes to which it has been added. Various techniques have been developed to hinder or delay the release of perfume from compositions so that they will remain aesthetically pleasing for a longer length of time. For example, see West German Patent 825,293, Dec. 17, 1951; East German Patent 15,693, Oct. 12, 1975; and U.S. Pat. Nos. 3,772,215, issued Nov. 13, 1973; and 3,567,119, issued Mar. 2, 1971. While such methods have been somewhat effective, there is still a need to economically formulate a composition which emits perfume from the composition and the treated surface even after product storage.

Encapsulation techniques have been used to enclose the perfume so that the fragrance is not emitted during storage and it is noticeable after actual use of the product, when the encapsulating material dissolves or breaks and the perfume is released. Storage of encapsulated perfume, though, can result in loss of the perfume stored within by capsule breakage and/or vaporization of the perfume core through the capsule wall.

Microencapsulation techniques are known for perfumes, medicines, adhesives, dyestuffs, inks, fertilizers, etc. See for example U.S. Pat. Nos. 4,446,032, Munteanu et al., issued May, 1984; 4,288,460, Ciliberto et al., issued Sept. 8, 1981; 4,268,411, Iwata et al., issued May 19, 1981 and 4,081,264, Ali, issued Mar. 28, 1978. Microencapsulation techniques and materials for forming microcapsules are disclosed in U.S. Pat. No. 2,800,458, Green, issued Jul. 23, 1957; U.S. Pat. Nos. 3,159,585, Evans et al., issued Dec. 1, 1964; 3,533,958, Yurkowitz, issued Oct. 13, 1970; 3,697,437, Fogle et al., issued Oct 10, 1972; 3,888,689, Maekawa et al., issued Jun. 10, 1975; U.S. Pat. No. 3,996,156, Matsukawa et al., issued Dec. 7, 1976; 3,965,033 Matsukawa et al., issued Jun. 22, 1976; 4,010,038, Iwasaki et al., issued Mar. 1, 1977; 4,016,098, Saeki et al., issued Apr. 5, 1977; 4,269,729, Maruyama et al., issued May 26, 1981; 4,303,548, Shimazaki et al., issued Dec. 1, 1981; 4,460,722, Igarashi et al., issued Jul. 17, 1984; 4,610,927, Igarahsi et al., issued Sept. 9, 1986; 4,961,871, Michael, issued Oct. 9, 1990; and Brit. Patent 1,483,542, published Aug 23, 1977.

Similarly, conditioning agents are known which promote the flow of solid particles. Some microencapsulation techniques have been developed which incorporate conditioning agents, such as silica particles, directly into the encapsulation material. See for example U.S. Pat. Nos. 4,268,411, issued May 19, 1981 and 4,288,460, issued Sep. 8, 1981. Although the incorporation of small particles into the perfume capsule wall is desirable to promote release by weakening the capsule wall, it Can also cause premature release of the perfume core during storage and/or handling.

It has now been found that adding silicon dioxide or aluminosilicate, which have a high adsorption efficiency, light density, water-insolubility, and/or a neutral or alkaline pH, to a wet cake containing perfume capsules, improves the fluidization and drying rate of the wet cake, and thereby enhances the flow and performance of the final perfume capsule composition. The silicon dioxide or aluminosilicate powder is believed to contribute the following advantages: (1) increases fluidization and drying rate of a wet cake, probably due to the increased interporosity and high adsorption efficiency of the powder; (2) protects perfume capsules from breakage by inhibiting contact between the perfume capsules; (3) acts as a scavenger for any perfume core which has inadvertently been released; (4) improves flow properties allowing better handling of the wet cake; and/or (5) reduces stress on the perfume capsule shell, allowing more of the capsules to be delivered without shell flaws.

SUMMARY OF THE INVENTION

The present invention covers a method for preparing perfume capsule compositions exhibiting improved physical and performance benefits, comprising:

(a) obtaining or preparing a slurry comprising, by weight, from about 5% to about 60% of perfume capsules and from about 40% to about 80% of water; said perfume capsules having an average particle size of between about 1 micron and about 450 microns and essentially consisting of a perfume core encapsulated by an outer coating; said perfume core being comprised of viscous perfume and perfume carrier;

(b) removing an amount of said water from said slurry sufficient to form a wet cake comprising, by weight, from about 15% to about 35% of water and from about 60% to about 85% of said perfume capsules;

(c) combining with said wet cake from about 0.1% to about 10%, by weight of said wet cake, of silicone dioxide or aluminosilicate particles having an average particle size of from about 0.1 micron to about 150 microns; and (d) removing an amount of water from the product of step (c) sufficient to form a free flowing composition comprising, by weight, from about 1% to about 15% water and from about 80% to about 99% of said perfume capsules.

DETAILED DESCRIPTION OF THE INVENTION

The present method comprises combining silicon dioxide or aluminosilicate with a wet cake containing perfume capsules to form a free flowing perfume capsule composition with enhanced performance properties. The component materials are described below.

A. Perfume Core

As used herein the term "perfume" is used to indicate any water-insoluble, pleasant smelling, odoriferous material characterized by a vapor pressure below atmospheric pressure at ambient temperatures. The perfume material will most often be liquid at ambient temperatures. A wide variety of chemicals are known for perfume uses, including materials such as aidehyde, ketones and esters. More commonly, naturally occurring plant and animal oils and exudates comprising complex mixtures of various chemical components are known for use as perfumes. The perfumes herein can be relatively simple in their compositions or can comprise highly sophisticated complex mixtures of natural and synthetic chemical components, all chosen to provide any desired odor and are compatible with the desired outer coating. Typical perfumes can comprise, for example, woody-/earthy bases containing exotic materials such as sandalwood oil, civet and patchouli oil. The perfumes can be of a light floral fragrance, e.g. rose extract, violet extract, and lilac. The perfumes can also be formulated to provide desirable fruity odors, e.g. lime, lemon and orange. Any chemically compatible material which exudes a pleasant or otherwise desirable odor can be used in the perfumed particles herein.

The viscous perfume together with a perfume carrier comprise the perfume core. The carrier materials employed herein are characterized by several criteria which make them especially suitable in the practice of this invention. Water soluble, toxicologically-acceptable, non-skin irritating, inert to the perfume, degradable and/or available from renewable resources, and relatively odorless carriers are used. In general, the carrier materials are solids at room temperature. This will prevent melting of the particles in storage. It is most desirable to have a carrier material that will not completely melt in an automatic dryer to avoid blocking of the lint screen and excessive build-up of heat in the dryer. The melting point of the carrier material should be compatible with the perfume in that it not be high enough to decompose the perfume.

In a preferred embodiment, the perfume carrier is a $C_{12}$–$C_{24}$, more preferably a $C_{14}$–$C_{20}$, most preferably a $C_{18}$ fatty alcohol.

Other carrier materials include fatty esters as described in U.S. Pat. No. 5,066,419, Walley et al., issued Nov. 19, 1991, the disclosure of which is incorporated herein by reference. Esters which are suitable for the present invention include, but are not limited to, $C_1$–$C_4$ alkyl esters of fatty acids, fatty acid esters of polyhydric alcohols, and fatty acid triglycerides and mixtures thereof.

B. Perfume Outer Coating Material

Compositions of the type described herein efficiently deliver their odor during actual use, i.e. during the washer cycle, dryer cycle or while storing or wearing an article of clothing.

Generally, the perfume core is surrounded or encapsulated by a perfume outer coating. The term encapsulate is used to describe a method of protecting a perfume fragrance/core. The perfume may be either a spray-dried emulsion of discrete microdroplets or a perfume/-core surrounded by a polymerized outer coating (capsule or shell) which is impervious to the materials in the perfume core and the materials which may come in contact with the outer surface of the shell. The outer coating can be composed of a wide variety of polymeric materials including polyurethane, polyolefin, polyamide, polyester, polysaccharide, silicone resins, and epoxy resins. Many of these types of polymeric materials are further described and exemplified in U.S. Pat. No. 3,879,542, Ida et al., issued Mar. 11, 1975, the disclosure of which is incorporated by reference.

Highly preferred materials for the outer coating are the aminoplast polymers comprising the reactive products of urea and aldehyde, e.g. formaldehyde. Such materials are those which are capable of acid condition polymerization from a water-soluble prepolymer state. The most preferred material is, methylene-N,N -bis(hydroxymethyl)-urea.

The outer coating can be a shell which can be gelatin, gum acacia, dextrin, modified food starch, wax, and hydroxypropyl cellulose, or mixtures thereof.

C. Silicon Dioxide or Aluminosilicate

In general, any water-insoluble silicon dioxide or aluminosilicate particle with high adsorption efficiency, small particle size relative to the microencapsulated perfume, and a neutral or alkaline pH can be used in the practice of this invention. Particularly preferred silicon dioxide powders are amphorous, fumed or precipitated silicon dioxides such as those which are available commercially and designated as Aerosil 972, Sipernat 50, and Sipernat 50S by Degussa Corp., of N.J. The hydrophobic, fumed silica, Aerosil R972 is most preferred.

Aluminosilicate ion exchange materials useful in the practice of this invention are commercially available. The aluminosilicates useful in this invention can be crystalline or amorphous in structure and can be naturally-occurring aluminosilicates or synthetically derived. A method for producing aluminosilicate ion exchange materials is discussed in U.S. Pat. No. 3,985,669, Krummel et al, issued Oct. 12, 1976, incorporated herein by reference. Preferred synthetic crystalline aluminosilicate ion exchange materials useful herein are available under the designations Zeolite A, Zeolite B, and Zeolite X. In an especially preferred embodiment, the crystalline aluminosilicate ion exchange material in Zeolite A and has the formula

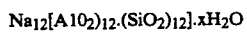

$$Na_{12}[AlO_2)_{12}.(SiO_2)_{12}]. xH_2O$$

wherein x is from about 20 to about 30, especially about 27.

The crystalline layered sodium silicates herein have the composition NaMSi$_x$Ohd 2x+1.yH$_2$O in which M denotes sodium or hydrogen, x is 1.9 to 4 and y is 0 to 20. These materials are described in U.S. Pat. No. 4,664,839, Rieck, issued May 12, 1987, incorporated herein by reference. In the above formula, M preferably represents sodium. Preferred values of x are 2, 3 or 4. Compounds having the composition NaMSi$_2$5.yH$_2$O are particularly preferred.

The most preferred commercially available aluminosilicate is Zeosyl 200 by J. M. Huber Corp., of Md.

The silicon dioxide or aluminosilicate should be from about 0.1% to about 10%, preferably from about 1% to about 7%, more preferably from about 2.5% to about 5%, based on the weight of the wet cake. The average particle size of the silicon dioxide or aluminosilicate is typically 0.1 micron to about 150 microns, more preferably from about 1 micron to about 50 microns. Where silicon dioxide is employed, it is the agglomerate or aggregate particle size which is considered, the agglomerate or aggregate particle being made up of silicon dioxide particles which are in the nanometer range. (See Degussa, "Technical Bulletin Pigments" No. 32, pp 8-9, 12-14).

In a highly preferred embodiment a wet cake containing perfume capsules and about from about 30% of water is combined with 5%, by weight of the wet cake, of silicon dioxide, with a aggregate particle size range between about 1 micron to about 50 microns.

D. The Method

First, a slurry comprising from about 5% to about 60%, preferably from about 20% to about 50%, most preferably from about 30% to about 40%, of perfume capsules is obtained or prepared. The perfume capsules have an average particle size of between about 1 micron and 450 microns, preferably between about 100 microns and about 200 microns. These perfume capsules essentially consist of a perfume core encapsulated by an outer coating. A variety of methods can be used to encapsulate the perfume core. As described above, the perfume core comprises a viscous perfume and a perfume carrier. Methods for encapsulation are well known to those skilled in the art. Microcapsules having the perfume core and polymer shell walls as described above can be prepared by any conventional process that produces capsules of the requisite size and shell thickness. Conservation and interfacial polymerization are methods which can be employed in a known manner to produce microcapsules of the desired characteristics. See for example U.S. Pat. Nos. 3,423,489, Arens et al., Jan. 21, 1969; 3,870,542, Ida et al., Mar. 11, 1975; 3,415,758, Dec. 10, 1968; 3,041,288, Anthony, Jun. 26, 1972, and 5,066,419, Walley et al., Nov. 19, 1991. All of these patents are incorporated herein by reference.

Perfume capsules with an outer coating made from the preferred urea-formaldeyde shell materials can be made by an interfacial polymerization process described more fully in U.S. Pat. No 3,516,941, Matson, Jun. 23, 1970, incorporated herein by reference.

No matter how the perfume capsules utilized herein are produced, a population range of between about 1 micron and about 450 microns, preferably an average size of about 150 microns should be obtained. Furthermore, the capsules utilized in the present invention generally have an average shell thickness ranging from about 0.1 micron to about 50 microns. Normally, capsules contain from about 10% to about 95%, more preferably from about 60% to about 85%, by weight of the capsule, of perfume core.

In a preferred embodiment the above described perfume capsules are prepared as a slurry containing about 70% water and a perfume capsule average particle size of from about 1 micron and about 450 microns, more preferably an average perfume capsule size about 150 microns.

Once the perfume capsules are present in the slurry, water can be removed using conventional methods. Such methods include filter belt drying, centrifuging, filter pressing, etc. Most preferably filter belt drying is used.

The second step herein is removing an amount of water from the above described slurry sufficient to form a wet cake comprising from about 15% to about 35%, preferably from about 20% to about 30%, of water and from about 60% to about 85%, preferably from about 70% to about 80%, of perfume capsules.

The third step of the method is combining the wet cake with from about 0.1% to about 10%, preferably from about 0.5% to about 7%, most preferably from about 2% to about 5%, by weight of the wet cake, of silicon dioxide or aluminosilicate having an average particle size of from about 0.1 micron to about 150 microns.

A preferred method is to remove a sufficient amount of water via a filter belt drier to form a wet cake containing from about 15% to about 35% water, preferably from about 22% to about 30% water and perfume capsules. To this wet cake from about 0.1% to about 10%, more preferably from 0. 5% to about 7%, most preferably from about 2% to about 5%, by weight of the wet cake, of silicon dioxide or aluminosilicate can be combined and mixed. Mixing can be accomplished by drum mixing, rotating, ribbon blending, baffled drum blending, etc. Preferably a drum or baffled drum is employed, since it gently but completely mixes the components without damaging the perfume capsules.

The final step is to remove water from the combined wet cake and silicon dioxide or aluminosilicate to form a free flowing composition comprising from about 1% to about 15% water, preferably from about 2% to about 10%, of water and from about 80% to about 99%, preferably from about 85% to about 95%, of perfume capsules. Conventional methods as described above to form the wet cake can be similarly utilized for this step.

The final product can be used alone or in combination to form a detergent composition, preferably a granular laundry detergent composition.

As used herein, all percentages, parts and ratios are by weight unless otherwise stated.

The following nonlimiting Examples illustrate the process of the invention and facilitate its understanding.

EXAMPLE I

The wet cake containing perfume capsules with various silicon dioxides and aluminosilicate are set forth in Table 1. The components are combined in a jar, gently shaken and assessed visually for fluidization (i.e. pourability).

TABLE 1

| | Weight % of Inqredients | | | | | | | | |
|---|---|---|---|---|---|---|---|---|---|
| | 1 | 2 | 3 | 4 | 5 | 6 | 7 | 8 | 9 |
| Perfume Wet Cake (1) | 90 | 95 | 97 | 95 | 96 | 97 | 95 | 93 | 90 |
| Zeosyle 200 (2) | 10 | 5 | | | | | | | |
| Aerosil 972 (3) | | | 3 | 5 | 4 | | | | |
| Sipernat 50 (4) | | | | | | 3 | 5 | 7 | 10 |
| Sipernat 50S (4) | | | | | | | | | |

| | 10 | 11 | 12 | 13 |
|---|---|---|---|---|
| Perfume Wet Cake (1) | 97 | 95 | 93 | 90 |
| Zeosyl 200 (2) | | | | |
| Aerosil 972 (3) | | | | |
| Sipernat 50 (3) | | | | |
| Sipernat 50S (3) | 3 | 5 | 7 | 10 |

(1) Wet cake containing 35.55% water and perfume capsules comprising a $C_{14}$ fatty alcohol perfume core and an outer coating of methylene-N,N-bis(hydroxymethyl-)urea.
(2) Zeosyl 200 is an aluminosilicate from J.M. Huber Corp.
(3) Aerosil 972, is a hydrophobic, fumed silicone dioxide from Degussa Corp.
(4) Sipernat 50 and Sipernat 50S are hydrophillic, precipitated silicon dioxides from Degussa Corp.

All of the samples exhibit enhanced initial fluidization over the wet cake alone. However, the samples with 3% Aerosil (#3) exhibits improved fluidization as compared to 3% Sipernat 50 (#6) and 3% Sipernat 50S (#10). 5% Sipernat 50 (#7) appears better than 5%

Sipernat 50S (#11), and 7% Sipernat 50S (#12) is slightly better than 7% Sipernat 50 (#8). Aerosil 972 is in excess when 5% Aerosil 972 (#4) is used.

Similar experiments using sodium sulfate, or sodium citrate do not exhibit similarly improved initial fluidization as seen with silicone dioxide or aluminosilicate.

EXAMPLE II

The wet cake containing perfume capsules and silicon dioxide used in the perfume capsule preparation process are set forth in Table 2. The conditioning agent is added to the wet cake, mixed and subject to ambient drying conditions. A can mixer is used to simulate drum mixing.

TABLE 2

|  | Weight % | | | |
|---|---|---|---|---|
|  | 14 | 15 | 16 | 17 |
| Wet Cake (1) | 97 | 95 | | |
| Aerosil 972 (2) | 3 | | | |
| Sipernat 50 (3) | | 5 | | |
| Wet Cake (4) | | | 95 | 93 |
| Sipernat 50S (3) | | | 5 | 7 |

(1) Wet cake containing 35.85% water and perfume capsules comprising a $C_{14}$ fatty alcohol perfume core and an outer coating of methylene-N,N-bis(hydroxymethyl-)urea.
(2) Aerosil 972 is a hydrophobic, fumed silicone dioxide from Degussa Corp.
(3) Sipernat 50 and Sipernat 50S are hydrophillic, percipitated silicon dioxides from Degussa Corp.
(4) Wet cake containing 26.14% water and perfume capsules comprising a $C_{14}$ fatty alcohol perfume core and an outer coating of methylene-N,N-bis(hydroxymethyl-)urea.

After mixing the perfume capsule wet cake with silicon dioxide for 5 minutes, the mixture is dried overnight at ambient drying conditions.

Overnight drying moisture levels are measured by Bidwell analysis, which is a standard moisture by solvent (kerosene) distillation procedure. Essentially, the Bidwell analysis consists of adding the same amount of solvent, such as kerosene, to a control having a known percentage of moisture and a sample as prepared herein. Distillation volumes are compared to determine percent moisture. Results are shown in Table 3.

TABLE 3

| | % Moisture as Measured by Bidwell | | | | | |
|---|---|---|---|---|---|---|
| Sample | 1 hr | 2 hr | 4 hr | 6 hr | 1st Overnight | 2nd Overnight |
| Wet Cake (1) | 36.47 | 32.23 | 30.24 | 26.29 | 14.22 | 4.58 |
| #14 | 32.17 | 31.68 | 26.87 | 22.33 | 6.44 | 4.17 |
| #15 | 33.83 | 32.38 | 27.72 | 25.0 | 11.24 | 4.87 |
| Wet Cake (3) | 24.72 | 25.19 | 10.38 | 18.39 | 10.59 | 3.10 |
| #16 | 24.76 | 24.43 | 20.68 | 13.43 | 8.50 | 2.34 |
| #17 | 28.59 | 28.36 | 22.32 | 23.45 | 13.41 | 3.59 |

(1) and (3) correspond to wet cakes set forth in Table 2.

Drying times of the wet cake under ambient conditions generally decrease when silicon dioxide is added.

Similar experiments using sodium citrate and sodium sulphate do not exhibit the same decreased drying times as seen with silicon dioxide (Samples 14–17).

Measurement using funnels with different diameter orifices is a standard means of determining flowability. The smallest orifice through which the material passes freely determines flowability. Before pouring the samples through the funnel, samples may be screened to remove lumps. Results are shown in Table 4.

TABLE 4

| | Funnel Flow | | |
|---|---|---|---|
| Sample | 6 hr | 1st overnight unscreened | 1st overnight screened |
| Wet Cake (1) | 5 | 5 | 5 |
| #14 | 5 | 4 | 2 |
| #15 | 5 | 4 | 2 |

(1) Corresponds to wet cake set forth in Table 2.

Addition of silicon dioxide or aluminosilicate enhances the fluidization/flowability of the perfume wet cake, allowing better handling in a mix drum without degrading.

The free flowing perfume capsule compositions of the present invention can be prepared in a variety of product forms, such as granules, powders, liquids, gels, pastes or they can be used alone. Such compositions are disclosed in U.S. Pat. Nos. 5,066,419, Walley et al., issued Nov. 19, 1991 and 4,145,184, Brain et al., issued Mar. 20, 1979.

A laundry detergent composition of the present invention comprises a sufficient amount of the free flowing perfume capsule composition to impart the desired fragrance, generally from about 0.1% to about 15%, from about 5% to about 50% of detergent surfactant, from about 5% to about 75% of detergent builders (optional, from about 5% to about 75% for granular compositions and from about 5% to about 50% for liquid compositions), and from about 1% to about 50% of other standard ingredients, such as enzymes, bleaches, fillers, dyes, and the like, can also be included.

EXAMPLE III

The following is an example of the use of the present free flowing perfume capsule composition in a granular laundry detergent.

| Component | Weight % |
|---|---|
| Sodium $C_{12}$ alkylbenzene sulfonate | 5.64 |
| Sodium Tallow alcohol sulfate | 2.42 |
| Sodium sulfate | 22.00 |
| Magnesium sulfate | 0.40 |
| Carboxymethyl cellulose | 0.29 |
| Etheylenediaminetetraacetic acid | 0.29 |
| Brightener | 0.15 |
| Sodium tripolyphosphate | 21.34 |
| $C_{14-15}$ alcohol polyethoxylate (E07) | 5.00 |
| Sodium perborate tetrahydrate | 13.23 |
| Sodium perborate monohydrate | 1.96 |
| Sodium carbonate | 7.00 |
| Proteolytic enzyme | 0.79 |
| Tetraacetylethylenediamine | 3.03 |
| Perfume Capsule Composition* | 1.00 |
| Water/minors | Balance |

*Prepared per Example II.

The above laundry detergent composition can be made using conventional methods. The perfume capsule composition can be combined with the other laundry detergent ingredients by mixing, preferably with the perfume capsule composition being added as one of the last ingredients.

EXAMPLE IV

A liquid laundry detergent composition herein is as follows.

The invention can be embodied in other specified forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range or equivalency of the claims are therefore intended to be embraced therein.

What is claimed is:

1. A method of preparing a perfume capsule composition comprising;
   (a) obtaining or preparing a slurry comprising, by weight, from about 5% to about 60% of perfume capsules and from about 40% to about 80% of water; said perfume capsules having an average particle size of between about 1 micron and about 450 microns and essentially consisting of a perfume core encapsulated by an outer coating; said perfume core being comprised of viscous perfume and perfume carrier;
   (b) removing an amount of said water from said slurry sufficient to form a wet cake comprising, by weight, from about 15% to about 35% of water and from about 60% to about 85% of said perfume capsules;
   (c) combining with said wet cake from about 0.1% to about 10%, by weight of said wet cake, of silicon dioxide or aluminosilicate particles having an average particle size of from about 0.1 micron to about 150 microns; and
   (d) removing an amount of water from the product of step (c) sufficient to form a free flowing composition comprising, by weight, from about 1% to about 15% water and from about 80% to about 99% of said perfume capsules.

2. The method of claim 1 wherein said outer coating of step (a) is a shell selected from the group consisting of gelatin, gum acacia dextrin, modified food starch, wax, hydroxypropyl cellulose, urea formaldehyde polymer; and mixtures thereof.

3. The method of claim 2 wherein said perfume carrier of step (a) is a water soluble $C_{12}$–$C_{24}$ fatty alcohol or fatty ester, or mixtures thereof.

4. The method of claim 3 wherein said wet cake of step (b) contains from about 22% to about 30% water.

5. The method of claim 4 wherein said silicon dioxide or aluminosilicate particles have an average particle size from about micron to about 50 microns.

6. The method of claim 5 wherein the silicon dioxide or aluminosilicate are combined with said wet cake by rotating, ribbon blending, drum mixing, or baffled drum blending.

7. The method of claim 6 wherein said wet cake of step (b) is formed by filter belt drying, centrifuging, or dry pressing.

8. The method of claim 7 wherein said water of step (d) is removed by filter belt drying, centrifuging or dry pressing.

9. The method of claim 8 wherein said perfume capsule outer coating of step (a) is methylene-N,N-bis(hydroxymethyl)urea.

10. The method of claim 9 wherein said particles of step (c) are fumed or precipitated.

11. The method of claim 9 wherein said perfume capsules of step (a) contain from about 10% to about 95%, by weight of the perfume capsule, of said perfume core.

12. The method of claim 11 wherein said wet cake of step (c) is combined with from about 2.5% to about 5%, by weight, of silicon dioxide or aluminosilicate particles.

13. The method of claim 12 wherein said perfume capsule of step (a) have an average particle size of about 150 microns.

14. The method of claim 13 wherein said perfume carrier of step (a) is a $C_{14}$–$C_{20}$ fatty alcohol.

15. The method of claim 14 wherein said perfume capsules of step (a) essentially consist of from about 60% to about 85%, by weight of the perfume capsule, of perfume core.

16. The method of claim 1 wherein said perfume capsules have an average particle size of about 100 to about 200 microns and said particles of step (c) are silicon dioxide particles having an average particle size of from about 1 micron to about 50 microns.

* * * * *

UNITED STATES PATENT AND TRADEMARK OFFICE
CERTIFICATE OF CORRECTION

PATENT NO. : 5,324,444
DATED : June 28, 1994
INVENTOR(S) : Gregory Berry et al

It is certified that error appears in the above-indentified patent and that said Letters Patent is hereby corrected as shown below:

Column 2, line 51, "silicone" should read "silicon".

Column 6, line 59, "(hydroxymethyl-)" should read "(hydroxymethyl)".

Column 7, line 26, "(hydroxymethyl-)" should read "(hydroxymethyl)".

Column 8, line 63 "EXAMPLE IV" is missing in its entirety.

UNITED STATES PATENT AND TRADEMARK OFFICE
CERTIFICATE OF CORRECTION

PATENT NO. : 5,324,444
DATED : June 28, 1994
INVENTOR(S) : Gregory Berry et al

It is certified that error appears in the above-indentified patent and that said Letters Patent is hereby corrected as shown below:

Column 8, line 66 the following information should be insert between "...herein is as follows." and "The invention can be ..."

| Component | Weight % |
|---|---|
| Monethanolammonium salt of $C_{12}$ linear alkyl benzene sulfonate | 18 |
| $C_{14-15}$ alcohol polyethoxylate (E07) | 33 |
| Monoethanolamine | 2 |
| Oleic acid | 1 |
| Ethanol | 5 |
| Colloidal silica | 2 |
| Perfume Capsule Composition* | 0.5 |
| Water/minors | Balance |

* Prepared as set forth in Example II.

Signed and Sealed this

Eighth Day of November, 1994

BRUCE LEHMAN

Attest:

Attesting Officer

Commissioner of Patents and Trademarks